US00PP19410P2

(12) United States Plant Patent
Nobuyuki

(10) Patent No.: US PP19,410 P2
(45) Date of Patent: Nov. 4, 2008

(54) ***PENTAS* PLANT NAMED 'DPRG'**

(50) Latin Name: *Pentas lanceolata*
Varietal Denomination: DPRG

(75) Inventor: Tanaka Nobuyuki, Aichi (JP)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 11/978,490

(22) Filed: Oct. 29, 2007

(51) Int. Cl.
*A01H 5/00* (2006.01)

(52) U.S. Cl. ..... Plt./466

(58) Field of Classification Search ..... Plt./466
See application file for complete search history.

*Primary Examiner*—Kent L Bell
(74) *Attorney, Agent, or Firm*—C. A. Whealy

(57) ABSTRACT

A new and distinct cultivar of *Pentas* plant named 'DPRG', characterized by its compact, upright and mounded growth habit; freely branching habit; freely flowering habit; double deep red-colored flowers that are held above the foliage on strong peduncles; and good garden performance.

1 Drawing Sheet

Botanical designation: *Pentas lanceolata.*
Cultivar denomination: 'DPRG'.

BACKGROUND OF THE INVENTION

The present invention relates to a new and distinct cultivar of *Pentas,* botanically known as *Pentas lanceolata* and hereinafter referred to by the name 'DPRG'.

The new *Pentas* is a product of a planned breeding program conducted by the Inventor in Aichi, Japan. The objective of the breeding program is to create new compact *Pentas* cultivars with double flowers.

The new *Pentas* originated from a cross-pollination made by the Inventor in March, 2002 in Aichi, Japan of a proprietary selection of *Pentas lanceolata* identified as code name D. Red, not patented, as the female, or seed, parent with a proprietary selection of *Pentas lanceolata* identified as code name D. Violet, not patented, as the male, or pollen, parent. The new *Pentas* was discovered and selected by the Inventor as a single flowering plant within the progeny of the stated cross-pollination in a controlled environment in Aichi, Japan in March, 2003.

Asexual reproduction of the new *Pentas* by cuttings in a controlled environment in Aichi, Japan since April, 2003, has shown that the unique features of this new *Pentas* are stable and reproduced true to type in successive generations.

SUMMARY OF THE INVENTION

The cultivar DPRG has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'DPRG'. These characteristics in combination distinguish 'DPRG' as a new and distinct cultivar of *Pentas:*

1. Compact, upright and mounded growth habit.
2. Freely branching habit.
3. Freely flowering habit.

4. Double deep red-colored flowers that are held above the foliage on strong peduncles.
5. Good garden performance.

Plants of the new *Pentas* can be compared to plants of the parent selections. Plants of the new *Pentas* differ from plants of the female parent selection in the following characteristics:

1. Plants of the new *Pentas* are more vigorous than plants of the female parent selection.
2. Plants of the new *Pentas* are more freely branching than plants of the female parent selection.
3. Plants of the new *Pentas* have thicker stems than plants of the female parent selection.
4. Plants of the new *Pentas* have larger leaves than plants of the female parent selection.

Plants of the new *Pentas* differ from plants of the male parent selection in the following characteristics:

1. Plants of the new *Pentas* have double flowers whereas plants of the male parent selection have single flowers.
2. Plants of the new *Pentas* and the male parent selection differ in flower color as plants of the male parent selection have violet-colored flowers.

Plants of the new *Pentas* can also be compared to plants of the *Pentas* cultivar New Look Violet, not patented. In side-by-side comparisons conducted in Bonsall, Calif., plants of the new *Pentas* differed from plants of the cultivar New Look Violet in the following characteristics:

1. Plants of the new *Pentas* were more compact than plants of the cultivar New Look Violet.
2. Plants of the new *Pentas* had double flowers whereas plants of the cultivar New Look Violet had single flowers.

BRIEF DESCRIPTION OF THE PHOTOGRAPHS

The accompanying colored photographs illustrate the overall appearance of the new *Pentas,* showing the colors as true as it is reasonably possible to obtain in colored reproductions of this type. Colors in the photographs may differ slightly from the color values cited in the detailed botanical description which accurately describe the colors of the new *Pentas*.

The photograph at the bottom of the sheet comprises a side perspective view of a typical plant of 'DPRG' grown in a container.

The photograph at the top of the sheet is a close-up view of typical flowers of 'DPRG'.

DETAILED BOTANICAL DESCRIPTION

The photograph and following observations, measurements and values describe plants grown in Bonsall, Calif. during the spring in a polyethylene-covered greenhouse and conditions which approximate commercial *Pentas* production. During the production of the plants, day temperatures ranging from 13° C. to 38° C. and night temperatures ranging from 13° C. to 21° C. Rooted young plants had been growing for about nine weeks when the photographs and description were taken. In the following description, color references are made to The Royal Horticultural Society Colour Chart, 1995 Edition, except where general terms of ordinary dictionary significance are used.

Botanical classification: *Pentas lanceolata* cultivar DPRG.

Parentage:

*Female, or seed, parent.*—Proprietary selection of *Pentas lanceolata* identified as code name D. Red. not patented.

*Male, or pollen, parent.*—Proprietary selection of *Pentas lanceolata* identified as code name D. Violet, not patented.

Propagation:

*Type.*—by cuttings.

*Time to initiate roots.*—About 20 days at 25° C.

*Time to produce a rooted young plant.*—About 30 days at 20° C.

*Root description.*—Fibrous, medium in thickness; brown in color.

*Rooting habit.*—Moderately freely branching; moderately dense.

Plant description:

*Plant and growth habit.*—Compact, upright and mounded growth habit. Freely branching habit with about four lateral branches developing per plant; dense and bushy habit. Moderately vigorous growth habit.

*Plant height.*—About 20 cm.

*Plant diameter.*—About 25 cm.

Lateral branch description:

*Length.*—About 17 cm.

*Diameter.*—About 4.5 mm.

*Internode length.*—About 3.2 cm.

*Aspect.*—Mostly upright.

*Texture.*—Pubescent.

*Color.*—146C.

Foliage description:

*Arrangement.*—Opposite; simple.

*Length.*—About 11 cm.

*Width.*—About 4.6 cm.

*Shape.*—Elliptic.

*Apex.*—Acuminate.

*Base.*—Attenuate.

*Margin.*—Entire.

*Texture, upper and lower surfaces.*—Pubescent, rough.

*Venation pattern.*—Pinnate; arcuate.

*Color.*—Developing and fully expanded foliage, upper surface: 147A; venation, 146C. Developing and fully expanded foliage, lower surface: 147B; venation, 147D.

*Petiole length.*—About 1.5 cm.

*Petiole diameter.*—About 2 mm.

*Petiole texture, upper and lower surfaces.*—Pubescent.

*Petiole color, upper surface.*—145B.

*Petiole color, lower surface.*—145A.

Flower description:

*Flower arrangement and habit.*—Star-shaped double flowers arranged on rounded terminal corymbs. Freely flowering habit with about 80 flowers per inflorescence. Flowers not persistent. Flowers face mostly upright.

*Fragrance.*—None detected.

*Natural flowering season.*—Plants flower continuously year round in Southern California. Early flowering habit, plants typically beginning flowering about four to six weeks after planting.

*Flower longevity.*—Individual flowers last about seven to ten days on the plant.

*Inflorescence height.*—About 4.4 cm.

*Inflorescence diameter.*—About 6 cm.

*Flower diameter.*—About 1.7 cm.

*Flower tube diameter.*—About 1 mm.

*Flower depth (height).*—About 2.4 cm.

*Flower tube length.*—About 1.5 cm.

*Flower bud.*—Shape: Elongated oblong. Length: About 2.2 cm. Diameter: About 5 mm. Color: 60A.

*Petals.*—Arrangement: Ten to twelve petals arranged in two whorls fused at the base in a slender tube. Lobe length: About 7 mm. Lobe width: About 3 mm. Lobe shape: Elliptic. Lobe apex: Acute. Lobe margin: Entire. Texture, upper surface: Smooth, glabrous. Texture, lower surface: Pubescent. Color: When opening, upper surface: More red than 60A. When opening, lower surface: 59D. Fully opened, upper surface: 60A; color becoming closer to 59B with development. Fully opened, lower surface: 60C; color becoming closer to 59C with development.

*Sepals.*—Arrangement: Five to six in a single whorl fused at the base; calyx, star-shaped. Length: About 4 mm to 9 mm. Width: About 1 mm to 2 mm. Shape: Lanceolate to narrowly elliptic. Apex: Acute. Margin: Entire. Texture, upper and lower surfaces: Pubescent. Color, upper surface: 147A. Color, lower surface: 147B.

*Peduncles.*—Length: About 6.4 cm. Diameter: About 3 mm. Strength: Strong. Texture: Pubescent. Color: 146B.

*Pedicels.*—Length: About 3 mm. Diameter: About 1 mm. Strength: Strong. Texture: Pubescent. Color: 145A.

*Reproductive organs.*—Stamens: None observed. Pistils: Quantity: One per flower. Pistil length: About 2.2 cm. Style length: About 1.5 cm. Style color: 145D. Stigma shape: Two-parted. Stigma color: 59A. Ovary color: 145B. Seed/fruit: Seed and fruit development have not been observed on plants of the new *Pentas*.

Garden performance: Plants of the new *Pentas* have been observed to have good garden performance and tolerate wind, rain and temperatures ranging from about 5° C. to about 30° C.

Pathogen/pest resistance: Plants of the new *Pentas* have been observed to be resistant to pathogens and pests common to *Pentas*.

It is claimed:

1. A new and distinct *Pentas* plant named 'DPRG' as illustrated and described.

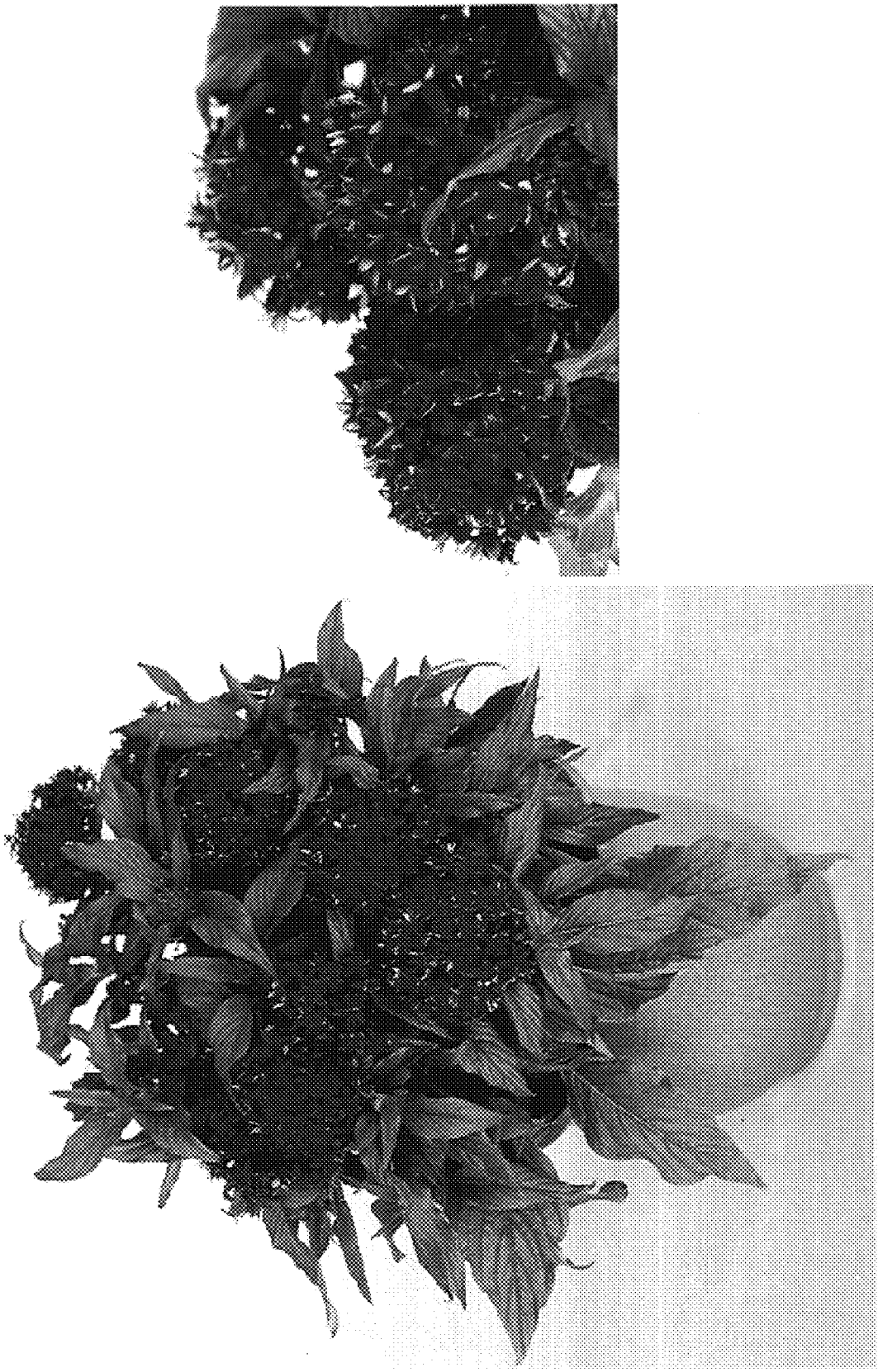

* * * * *